US00PP19433P2

(12) United States Plant Patent
Radler

(10) Patent No.: US PP19,433 P2
(45) Date of Patent: Nov. 11, 2008

(54) CLIMBING ROSE PLANT NAMED 'RADMOR'

(50) Latin Name: *Rosa hybrida*
Varietal Denomination: Radmor

(75) Inventor: William J. Radler, Greenfield, WI (US)

(73) Assignee: CP Delaware, Inc., Wilmington, DE (US)

( * ) Notice: Subject to any disclaimer, the term of this patent is extended or adjusted under 35 U.S.C. 154(b) by 0 days.

(21) Appl. No.: 11/907,285

(22) Filed: Oct. 10, 2007

(51) Int. Cl.
*A01H 5/00* (2006.01)

(52) U.S. Cl. ..... Plt./114

(58) Field of Classification Search ..... Plt./114
See application file for complete search history.

*Primary Examiner*—Annette H Para
*Assistant Examiner*—S. B. McCormick-Ewoldt
(74) *Attorney, Agent, or Firm*—Buchanan Ingersoll & Rooney PC

(57) ABSTRACT

A new and distinct variety of rose plant is provided which forms in abundance on a substantially continuous basis attractive cuplike semi-double blossoms that are soft pink and finish to shell pink in coloration. The vegetation is vigorous and the growth habit is upright and climbing. Attractive ornamental green foliage having a semi-glossy appearance is formed. Excellent resistance with respect to blackspot is displayed. The hardiness of the new variety is excellent for a climber. The new variety is particularly well suited for growing as distinctive ornamentation in parks, gardens, and residential settings.

1 Drawing Sheet

Botanical/commercial classification: *Rosa hybrida*/ Climbing Rose Plant.
Varietal denomination: cv. Radmor.

SUMMARY OF THE INVENTION

The new variety of *Rosa hybrida* climbing rose plant of the present invention was created at Greenfield, Wis., U.S.A., by artificial pollination wherein two parents were crossed which previously had been studied in the hope that they would contribute the desired characteristics. The female parent (i.e., the seed parent) was the 'Radsbs' variety (non-patented in the United States). The male parent (i.e., the pollen parent) of the new variety was a salmon-colored Rugohybrid of the 'Radspot' variety (non-patented in the United States). The 'Radspot' variety is a seedling of the 'Radbrite' variety (U.S. Plant Pat. No. 17,391). The parentage of the new variety can be summarized as follows:

'Radsbs'×'Radspot'.

The seeds resulting from the above pollination were sown and small plants were obtained which were physically and biologically different from each other. Selective study resulted in the identification of a single plant of the new variety.

It was found that the new climbing rose plant of the present invention possesses the following combination of characteristics:

(a) abundantly and substantially continuously forms attractive semi-double cuplike blossoms that are soft pink and finish to a shell pink coloration, (b) exhibits an upright and climbing growth habit, (c) forms vigorous vegetation, (d) abundantly forms attractive ornamental green foliage with a semi-glossy appearance, (e) exhibits excellent resistance to blackspot, and (f) exhibits excellent cold hardiness.

The new variety displays a good repeat blooming character and its winter hardiness is outstanding for a climbing rose plant. The growth is very vigorous and the canes commonly are of medium to heavy caliper for the class.

The new variety well meets the needs of the horticultural industry. It can be grown to advantage as attractive ornamentation in parks, gardens, public areas, and in residential settings. It alternatively can be trimmed and grown as a compact rose bush in the absence of support. The new variety is particularly well suited for providing attractive ornamentation in the landscape. The pink blossoms contrast nicely with the semi-glossy green foliage.

The new variety of the present invention can be readily distinguished from its ancestors. Unlike the new variety the 'Radsbs' variety displays a more bushy growth habit and forms smaller blossoms having more petals which are a yellow blend in coloration. Also, the 'Radsbs' variety tends to be somewhat less winter hardy than the new variety. The 'Radbrite' variety displays dissimilar salmon-pink blossoms with a yellow eye. The overall coloration of the new variety is much lighter and softer and is lacking a yellow eye.

The characteristics of the new variety have been found near West Grove, Pa., U.S.A. and elsewhere, to be homogeneous and stable and to be strictly transmissible by asexual propagation, such as budding, grafting, and the rooting of cuttings from one generation to another. The new variety reproduces in a true-to-type manner by such asexual propagation.

The new variety has been named 'Radmor' and is being marketed under the MORNING MAGIC trademark.

BRIEF DESCRIPTION OF THE PHOTOGRAPH

The accompanying photograph shows, as nearly true as it is reasonably possible to make the same in a color illustration of this character, a typical specimen of the new variety. A mature flowering plant is shown during the summer while growing on a support at Greenfield, Wis., U.S.A.

DETAILED DESCRIPTION

The chart used in the identification of colors is that of The Royal Horticultural Society (R.H.S. Colour Chart), London, England. The description is based on the observation of three-year-one specimens of the new variety during September while growing outdoors on their own roots near West Grove, Pa., U.S.A.

Class: Climbing Rose.

Plant:

*Height.*—Approximately 4 to 5 feet on average at the end of the growing season, and commonly assumes a mature height of approximately 8 feet.

*Width.*—Approximately 3 to 4 feet on average at the end of one growing season, and commonly continues to display. Approximately the same width at full maturity.

*Habit.*—Upright and climbing.

Branches:

*Color.*—Young stems: commonly between Green Group 139B and Yellow-Green Group 144A sometimes lightly blushed with Greyed-Purple Group 183B and Greyed-Purple Group 187B when exposed to the sun. Adult wood: near Yellow-Green Group 148A.

*Texture.*—Young stems: smooth. Adult wood: smooth.

*Caliper.*—Canes are medium to heavy for the class.

*Thorns.*—On young stems: commonly bear several large almost straight prickles which are approximately 0.9 to 1.3 cm in length on average having a somewhat narrow moderately long base that is approximately 8 mm in length and approximately 5 mm in width, as well as a few small prickles, having a coloration between Greyed-Yellow Group 161A and Greyed-Orange Group 164B and often lightly suffused with Greyed-Red Group 181A and Greyed-Purple Group 184B. On mature wood: commonly bear large prickles similar to those on young stems, as well as a few small prickles, having a coloration between Greyed-Orange Group 164A and Greyed-Orange Group 165A.

Leaves:

*Leaflet number.*—3, 5, and 7.

*Leaflet texture.*—Moderately rugose, and with a semi-glossy finish.

*Leaflet size.*—Commonly approximately 4 to 5 cm in length on average, and approximately 3 to 4 cm in width on average at the widest point:

*Leaflet shape.*—Oval to somewhat ovate with acute to somewhat acuminate apices, and rounded bases.

*Leaflet margins.*—Serrulate.

*Leaf size.*—Commonly approximately 9.5 to 14.5 cm in length on average, and approximately 10.5 cm in width on average at the widest point.

*Overall appearance.*—Very abundant, and medium green with a semi-glossy finish.

*Color.*—Young leaves: upper surfaces commonly are between Green Group 139A and Yellow-Green Group 147A and sometimes lightly suffused with near Greyed-Purple Group 183B and Greyed-Purple Group 187C, and under surfaces commonly are between Green Group 139C and Yellow-Green Group 147B and moderately suffused with near Greyed-Purple Group 183B and Greyed-Purple Group 187C. Mature leaves: upper surfaces commonly are between Green Group 139A and Yellow-Green Group 147A, and under surfaces commonly are between Yellow-Green Group 147B and 147C.

*Stipules.*—Configuration: commonly possess moderately narrow medium to long points that turn out of an angle of more than 45 degrees. Length: commonly approximately 2 to 2.5 cm. Width: commonly approximately 0.8 cm at the widest portion of the body. Coloration: near Green Group 138A.

*Petiole.*—Length: commonly approximately 3.7 cm on average. Diameter: commonly approximately 2 mm on average. Texture: slightly bristling. Color: Green Group 138A.

*Rachis.*—Average in caliper, the upper surface commonly is moderately grooved with some stipitate glands and tiny hairs on the edges of the grooves, and the underside commonly is rough with a few stipitate glands and numerous small prickles.

Inflorescence:

*Peduncle.*—Bearing: typically erect and very strong. Diameter: commonly approximately 3 mm. Texture: moderately smooth with some stipitate glands and a few hairs. Color: commonly between Yellow-Green Group 144B and 144C, and sometimes moderately suffused with between Greyed-Purple Group 183B and 183C.

*Sepals.*—Length: commonly approximately 2.5 cm on average. Width: commonly approximately 1 cm on average. Extensions: commonly absent. Texture: the inner surface is lined and edged with very line wooly tomentum, and the margins commonly are lined with a few stipitate glands and hairs. Apex: acute. Color: commonly near Yellow-Green Group 144A fading to Yellow-Green Group 144C. Number: five.

*Buds.*—Shape: commonly very pointed to urn-shaped as the calyx breaks. Length: as the calyx breaks commonly approximately 2 to 3 cm on average. Diameter: as the calyx breaks commonly approximately 2 to 2.5 cm at the widest point. Texture: commonly bears numerous stipitate glands and some hairs. Color (as the calyx breaks): commonly between Yellow-Green Group 144A and 144B and often moderately suffused with Greyed-Purple Group 183B and 183C.

*Flower.*—Form: semi-double and cup-shaped. Configuration: when partially opened high-centered with the petals being somewhat loosely spiraled and the petals edges being somewhat slightly reflexed outwards, and when fully opened cup-shaped to somewhat flat and the petal edges being flat to undulated and very slightly reflexed outward, with the inner petals being crinkled/ruffled. Diameter: commonly approximately 8.5 to 9 cm on average when fully open. Bearing: commonly in clusters of up to approximately 5 blooms per cluster, with the clusters being irregularly rounded and borne on medium to long stems having lengths of approximately 20 to 30 cm. Color (when opening begins): Upper surface: Red Group 48D and Red Group 50C, and at the base near Yellow Group 12B. Under surface: near Red Group 36A and Red Group 37B, and at the base near Yellow-Orange Group 19C. Color (when blooming): Upper surface: Red Group 50D and Red Group 51D, near the base Yellow Group 3D and Yellow Group 10C, and at the point of attachment Yellow Group 12B. Under surface: near Red Group 36D and 36B towards the apex. Color (at end of blooming) upper surface: near Red Group 36B, and at the area of attachment a moderately large zone of White Group 155B with a hint of Yellow-Orange Group 20D at the central base portion. Under surface: substantially uniformly Red Group 36B with some White Group 155B towards the base. Lastingness: commonly approximately 4 to 5 days or more on the plant, depending upon environmental conditions, and approximately 4 to 5 days when cut and placed in a vase. Fragrance: strong citrus-rose. Petal form: substantially round to very broadly obovate. Petal number: commonly approximately 10 to 14 on average. Petal apex: commonly rounded and sometimes notched with one or two notches. Petal size: commonly approximately 4.5 cm on average in length and width. Petal texture: medium to thick in substance, the upper surfaces commonly are moderately velvety to slightly satiny in appearance, and the under surfaces are mostly satiny to somewhat satiny. Petaloid number: commonly approximately 1 to 2 on average per flower and arranged irregularly. Petaloid length: commonly approximately 3.4 cm on average. Petaloid width: commonly approximately 1.1 cm at the widest point. Petaloid color: near Yellow Group 7A. Petal drop: very good, the petals commonly drop cleanly and freely. Stamen number: approximately 165 to 170 on average arranged regularly about the pistils. Anthers: approximately 1 mm in size. Anther color: commonly between Yellow Group 13C and Yellow-Orange Group 16A when immature, and between Greyed-Orange Group 163A and Greyed-Orange Group 165A when mature. Filament length: medium to long, and commonly approximately 7 to 12 mm, and most bear anthers. Filament color: Yellow Group 13C and sometimes moderately suffused with Red Group 43C. Pollen: commonly is present in a moderate to abundant quantity and commonly is near Yellow Group 13B in coloration. Pistils: separate and free, and commonly approximately 40 on average. Stigma color: commonly between Yellow Group 8D and Yellow Group 9D. Styles: moderately uneven in length, commonly approximately 4.5 mm in length, and approximately 0.25 mm in diameter. Style color: commonly near Yellow Group 8D suffused with Red Group 46D. Ovaries: typically enclosed in the calyx.

*Hips.*—Oblate in shape, approximately 18 mm in length on average, approximately 12 mm in width on average, possess a smooth surface with thick fleshy walls, the sepals commonly persist, and commonly Orange-Red Group 30C and 30D in coloration.

*Seeds.*—Medium in size, and commonly number approximately 3 to 6 per hip.

Development:

*Vegetation.*—Vigorous.

*Blossoming.*—Very abundant and substantially continuous during the growing season.

*Resistance to diseases.*—Excellent with respect to blackspot, and powdery mildew when compared to commercial rose varieties being grown under comparable conditions near West Grove, Pa., U.S.A.

*Cold hardiness.*—Excellent, and has proven to be completely winter hardy in U.S.D.A. Hardiness Zone No. 5.

*Formation of hips/seeds.*—Good.

The new 'Radmor' variety has not been observed under all possible environmental conditions to date. Accordingly, it is possible that the phenotypic expression may vary somewhat with changes in light intensity and duration, cultural practices, and other environmental conditions.

I claim:

1. A new and distinct climbing rose plant characterized by the following combination of characteristics:

(a) abundantly and substantially continuously forms attractive semi-double cuplike blossoms that are soft pink and finish to shell pink in coloration, (b) exhibits an upright and climbing growth habit, (c) forms vigorous vegetation, (d) abundantly forms attractive ornamental green foliage with a semi-glossy appearance, (e) exhibits excellent resistance to blackspot, and (f) exhibits excellent cold hardiness;

substantially as herein shown and described.

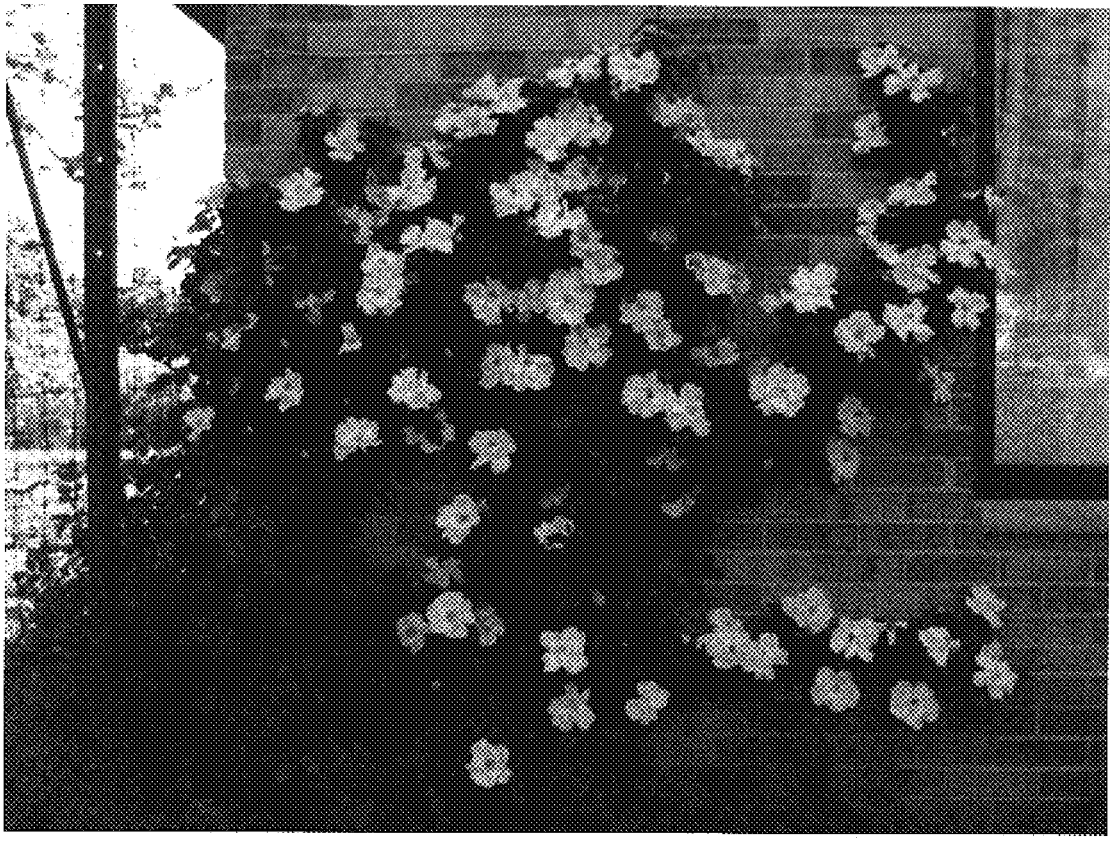

* * * * *